United States Patent [19]

Aldrich et al.

[11] 4,002,767
[45] Jan. 11, 1977

[54] 1-TERTIARY-ALKYL-3-(SUBSTITUTED CYCLOHEXENYL)UREAS AS ANTIHYPERTENSIVE AGENTS

[75] Inventors: Paul E. Aldrich, Wilmington, Del.; Gilbert H. Berezin, West Chester, Pa.; Bruce I. Dittmar, Wilmington, Del.

[73] Assignee: E. I. Du Pont de Nemours and Company, Wilmington, Del.

[22] Filed: Mar. 11, 1975

[21] Appl. No.: 555,308

Related U.S. Application Data

[63] Continuation-in-part of Ser. No. 525,445, Nov. 20, 1974, abandoned, which is a continuation-in-part of Ser. No. 461,697, April 17, 1974, abandoned.

[52] U.S. Cl. .......................... 424/322; 260/553 R

[51] Int. Cl.² ........................................ A61K 31/17
[58] Field of Search ................ 260/553 R; 424/322

[56] References Cited

UNITED STATES PATENTS

| | | | |
|---|---|---|---|
| 3,385,693 | 5/1968 | Cuckenbaugh | 71/120 |
| 3,701,807 | 10/1972 | Chupp | 260/553 A |

*Primary Examiner*—Leonard Schenkman

[57] ABSTRACT

1-Tertiary-alkyl-3-(substituted cyclohexenyl)ureas that exhibit antihypertensive activity in warm-blooded animals. A representative compound is 1-tert-butyl-3-(3-oxo-1-cyclohexen-1-yl)urea.

15 Claims, No Drawings

1-TERTIARY-ALKYL-3-(SUBSTITUTED CYCLOHEXENYL)UREAS AS ANTIHYPERTENSIVE AGENTS

CROSS-REFERENCE TO RELATED APPLICATION

This application is a continuation-in-part of our copending application Ser. No. 525,445, filed Nov. 20, 1974, which in turn is a continuation-in-part of our application Ser. No. 461,697, filed Apr. 17, 1974, both now abandoned.

BACKGROUND OF THE INVENTION

Certain guanidine derivatives of tert-carbinamines possess antihypertensive (hypotensive) activity. Specific examples are tert-alkyl cyanoguanidines such as 1-tert-amyl-3-cyanoguanidine as described in S. M. Gadekar, S. Nibi, and E. Cohen, J. Med. Chem., 11 811 (1968); and various derivatives of tert-butyl guanidines, as described in J. H. Short, C. W. Ours, W. J. Ranuse, Jr., J. Med. Chem., 11 1129 (1968).

Urea derivatives, however, are not represented in comprehensive discussions of antihypertensive agents. These discussions include W. T. Comer and A. W. Gomoll, Medicinal Chemistry, Third Edition, A. Burger, Wiley-Interscience, New York, 1970, pp. 1019–1064; and Medicinal Chemistry, Volume 7, "Antihypertensive Agents," E. Schlittler, Academic Press, New York, 1967. The urea-derivative compounds of this invention provide effective treatment of hypertension, yet differ structurally and chemically over currently known anithypertensive agents.

SUMMARY OF THE INVENTION

According to this invention there is provided compounds represented by the formula

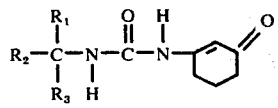

where
$R_1$, $R_2$ and $R_3$ are $C_1$–$C_3$ alkyl, $C_2$–$C_3$ alkenyl; with the provisos that the total numer of carbon atoms of $R_1$, plus $R_2$, plus $R_3$ does not exceed 5, and that two of $R_1$, $R_2$ and $R_3$ may be joined to form a cycloalkyl or cycloalkenyl group or suitable pharmaceutical salts of these compounds, such as sodium, potassium, and calcium.

This invention also includes pharmaceutical compositions containing these compounds and methods of using them.

DETAILED DESCRIPTION

Preferred Compounds

The antihypertensive compounds most preferred because of their high level of antihypertensive activity are:
1-tert-butyl-3-(oxo-1-cyclohexen-1-yl)urea
1-tert-amyl-3-(3-oxo-1-cyclohexen-1-yl)urea
1-(1-methylcyclopentyl)-3-(3-oxo-1-cyclohexen-1-yl)urea.

SYNTEHSIS

The compounds of this invention are readily prepared as represented by the following equation:

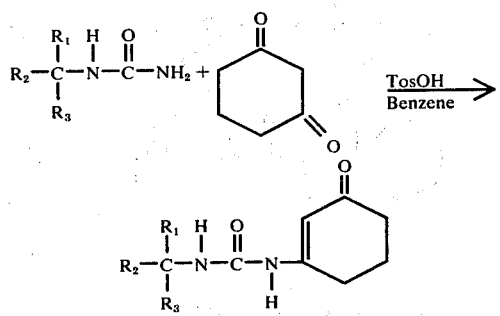

Reactants are heated at reflux in benzene with catalysis of p-toluenesulfonic acid. The water removal through the refluxing procedure yields the compound product.

The salts of the compounds of this invention can be prepared by treating the compound with an alcoholic or aqueous solution of an equimolar amount of the respective alkali hydroxide and evaporating to dryness. In general, because the salts of these compounds hydrolyze readily, such salts are less desirable for use in formulating pharmaceutical compositions of the invention than the compounds per se.

EXAMPLE 1

1-tert-butyl-3-(3-oxo-1-cyclohexen-1-yl)urea

To a solution of 11.2 g of 1,3-cyclohexanedione in 250 ml of benzene is added 11.6 g tert-butylurea and 100 mg of p-toluenesulfonic acid. The solution is heated at reflux under nitrogen with water removal for three hours. At the end of this period the solution is cooled and the precipitated product removed by filtration. The precipitate is recrystallized from acetonitrile to give 14 g of 1-tert-butyl-3-(3-oxo-1-cyclohexene-1-yl)urea, m.p. 223°–225° C.

The infrared and n.m.r. spectra are consistent with the assigned structure.

EXAMPLES 2–9

Using the procedure described in Example 1, the reactants shown in column 1 produce the respective products as shown in column 2.

| Example | Reactants | Products |
|---|---|---|
| 2 | $H_3C-CH_2-\underset{CH_3}{\overset{CH_3}{\underset{|}{\overset{|}{C}}}}-NHCONH_2$ + [cyclohexanedione] | $H_3C-CH_2-\underset{CH_3}{\overset{CH_3}{\underset{|}{\overset{|}{C}}}}-NH\overset{O}{\overset{\|}{C}}-\underset{H}{N}$-[3-oxocyclohexenyl] |

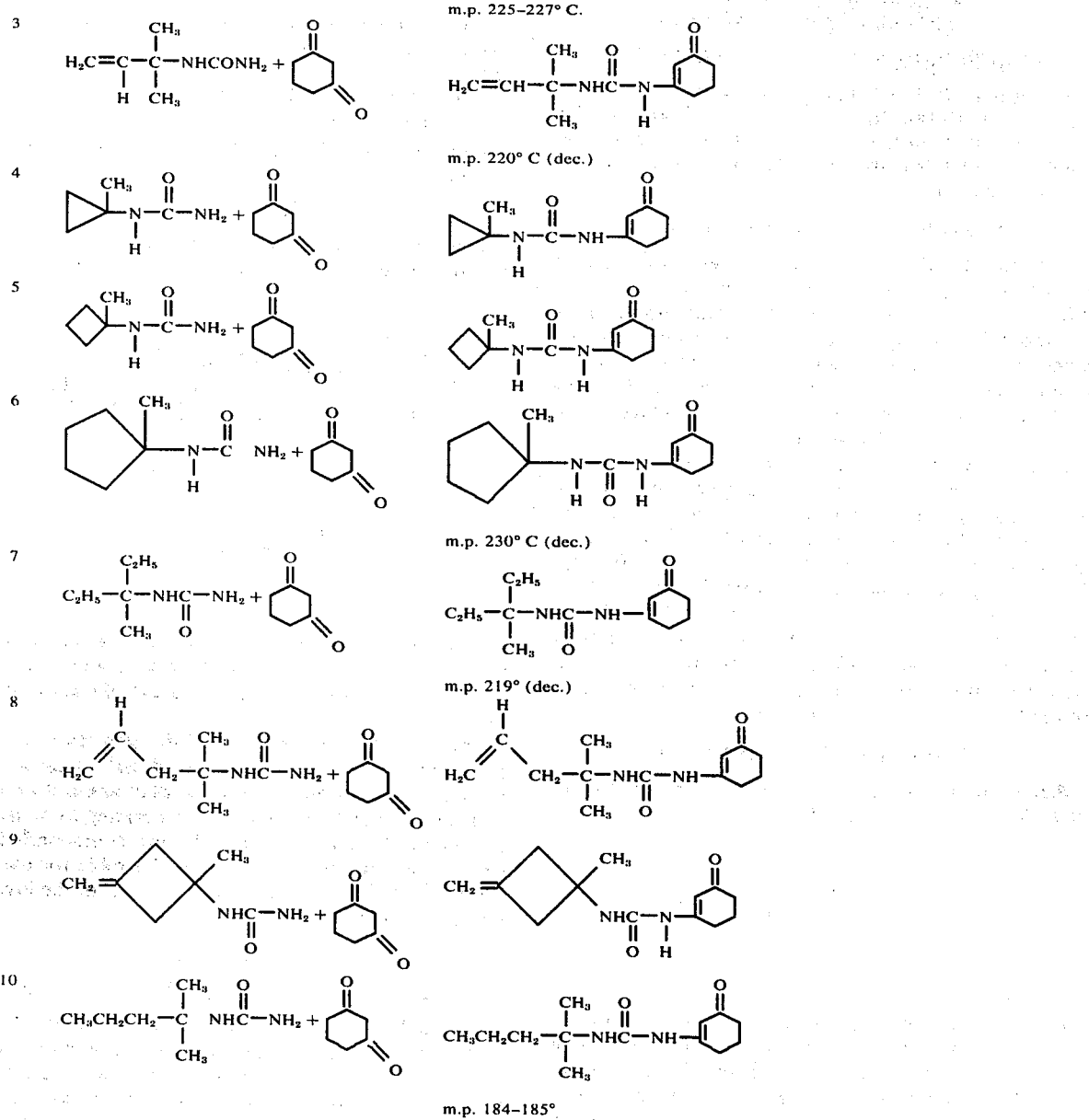

The compounds of this invention can be administered in the treatment of hypertension by any means that effects contact of the active ingredient compound with the site of action in the body of a warm-blooded animal. For example, administration can be parenteral, i.e., subcutaneous, intravenous, intramuscular, or intraperitoneal; alternatively or concurrently, administration can be by the oral route.

For the purpose of this disclosure, a warm-blooded animal is a member of the animal kingdom possessed of a homeostatic mechanism and includes mammals and birds.

The dosage administered is dependent on the age, health, and weight of the recipient, the extent of disease, kind of concurrent treatment, frequency of treatment and the effect desired. Usually, a daily dosage of active ingredient compound can be from about 0.1 to 50 milligrams per kilogram of body weight. Ordinarily, from 0.5 to 40, and preferably 1.0 to 20, milligrams per kilogram per day administered in one or more doses daily is effective to obtain desired results. For the more potent compounds of the invention, e.g., 1-(1-methylcyclopentyl)-3-(3-oxo-1-cyclohexen-1-yl)urea, 1-tert-butyl-3-(3-oxo-1-cyclohexen-1-yl)urea and 1-tert-amyl-3-(3-oxo-1-cyclohexen-1-yl)urea, the daily dosage ranges are from about 0.1 to 20 mg/kg, preferably 0.5 to 15 mg/kg, and more preferably 1.0 to 10 mg/kg.

The antihypertensive activity of the compounds of this invention is evidenced by tests conducted in hypertensive rats and by further tests which show a blood pressure lowering effect in normotensive dogs.

In these tests rats are made hypertensive by repeated injections of desoxycorticosterone acetate (DOCA) and by giving the rats saline solution to drink essentially according to the method described by Stanton and White [Arch. Intern. Pharmacodyn., 154, 351 (1957)].

Graded dose levels of each compound are administered orally to groups of eight hypertensive rats. The compound is prepared in an aqueous polyvinyl alcohol/acacia vehicle and administered at a volume to body weight ratio of 5.0 ml/kg. Sixteen hypertensive rats receiving the aqueous vehicle by the same route serve as controls for each test. At various intervals of time after treatment, usually 90 minutes, the systolic arterial blood pressure of each rat is determined by a modification of the microphone-manometer technique [Friedman, M. and Freed, S. C., Proc. Soc. Exp. Biol. and Med., 70, 670 (1959)]. That dose of compound which produces a 30 mm mecury (mm Hg) reduction in blood pressure when compared to the mean systolic arterial blood pressure of the control animals is then determined (Effective Dose 30). For example, an ED30 of 15 mg/kg orally was obtained with 1-tert-butyl-3-(3-oxo-1-cyclohexen-1-yl)urea; an ED30 value of 8.5 mg/kg was obtained orally with 1-(1-methylcyclopentyl)-3-(3-oxo-1-cyclohexen-1-yl)urea.

In a test involving dogs, these compounds are administered intravenously (i.v.) to eight anesthetized normotensive dogs according to a cumulative dose schedule. Arterial blood pressure is recorded directly through an arterial cannula and a polygraph by which it is determined that the compound shows statistically significant blood pressure lowering in comparison to the predosing control value and to the effect of vehicle on control animals.

The compounds of this invention can be employed in useful pharmaceutical compositions in such dosage forms as tablets, capsules, powder packets, liquid solutions, suspensions or elixirs for oral administration; liquid for parenteral use, and in certain cases, suspensions for parenteral use. In such compositions, the active ingredient will ordinarily be present in an amount of at least 0.5% by weight based on the total weight of the composition and not more than 95% by weight.

Besides the active ingredient compound of this invention, the antihypertensive composition can contain a solid or liquid non-toxic pharamaceutical carrier for the active ingredient.

The capsules, tablets, and powders will generally constitute from about 1 to about 95% and preferably from about 5 to 90% by weight of active ingredient. These dosage forms preferably contain from about 5 milligrams to about 500 milligrams of active ingredient, with about 7 milligrams to about 250 milligrams most preferred.

The pharmaceutical carrier can be a sterile liquid such as water, or a suitable oil, including those of petroleum, animal, or vegetable oil of synthetic origin, for example, peanut oil, soybean oil, mineral oil, sesame oil, and the like. In general, water, saline, aqueous dextrose (glucose), and related sugar solutions and glycols such as propylene glycol and polyethylene glycols are preferred liquid carriers, particularly for injectible solutions. Sterile injectible solutions will ordinarily contain from about 0.5 to about 25% and preferably about 1 to about 10% by weight of the active ingredient.

Oral administration can be in a suitable suspension or syrup, in which the active ingredient ordinarily will constitute from about 0.7 to about 10% and preferably about 1 to about 5% by weight. The pharmaceutical carrier in the composition can be an aqueous vehicle such as an aromatic water, a syrup, or a pharmaceutical mucilage.

Suitable pharmaceutical carriers are described in "Remington's Pharmaceutical Sciences" by E. W. Martin, a well-known reference text in this field.

The following examples will further illustrate the preparation of pharmaceutical compositions of the invention.

EXAMPLE A

A large number of unit capsules are prepared by filling standard two-piece hard gelatin capsules each with 250 milligrams of powdered 1-tert-butyl-3-(3-oxo-1-cyclohexen-1-yl)urea, 110 milligrams of lactose, 32 milligrams of talc, and 8 milligrams stearate.

EXAMPLE B

A mixture of 1-(1-methylcyclopentyl)-3-(3-oxo-1-cyclohexen-1-yl)urea in soybean oil is prepared and injected by means of a positive displacement pump into gelatin to form soft gelatin capsules containing 35 milligrams of the active ingredient. The capsules are washed in petroleum ether and dried.

EXAMPLE C

A large number of tablets are prepared by conventional procedures so that the dosage unit is 100 milligrams of active ingredient, 7 milligrams of ethyl cellulose, 0.2 milligrams of colloidal silicon dioxide, 7 milligrams of magnesium stearate, 11 milligrams of microcrystalline cellulose, 11 milligrams of cornstarch and 98.8 milligrams of lactose. Appropriate coatings may be applied to increase palatability or delay absorption.

EXAMPLE D

A parenteral composition suitable for administration by injection is prepared by stirring 1.5% by weight of 1-tert-butyl-3-(3-oxo-1-cyclohexen-1-yl)urea in 10% by volume propylene glycol and water. The solution is sterilized by filtration.

EXAMPLE E

An aqueous suspension is prepared for oral administration so that each 5 milliliters contain 50 milligrams of finely divided 1-tert-butyl-3-(3-oxo-1-cyclohexen-1-yl)urea, 500 milligrams of acacia, 5 milligrams of sodium benzoate, 1.0 grams of sorbitol solution, U.S.P., 5 milligrams of sodium saccharin, and 0.025 milliliters of vanilla tincture.

EXAMPLE F

A parenteral composition suitable for administration by injection is prepared by dissolving 1% by weight of 1-tert-amyl-3-(3-oxo-1-cyclohexen-1-yl)urea in sodium chloride injection U.S.P. XV and adjusting the pH of the solution to between 6 and 7. The solution is sterilized by filtration.

A wide variety of compositions included within this invention can be prepared by substituting other compounds embraced by this invention for the specific compounds named in Examples A–F above and substituting other suitable pharmaceutical carriers described in "Remington's Pharmaceutical Sciences".

What is claimed:
1. A compound of the formula

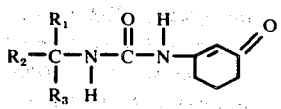

where
R₁, R₂, and R₃ = $C_1$–$C_3$ alkyl, $C_2$–$C_3$ alkenyl, or two of R₁, R₂, and R₃ may be joined to form a cycloalkyl or cycloalkenyl group; and its suitable pharmaceutical salts;

provided that the total number of carbon atoms of R₁ + R₂ + R₃ does not exceed 5.

2. The compounds of claim 1 wherein R₁, R₂, and R₃ independently = $C_1$–$C_3$ alkyl.

3. The compound of claim 1 which is 1-tert-butyl-3-(3-oxo-1-cyclohexen-1-yl)urea.

4. The compound of claim 1 which is 1-tert-amyl-3-(3-oxo-1-cyclohexen-1-yl)urea.

5. The compound of claim 1 which is 1-(1-methylcyclopentyl)-3-(3-oxo-1-cyclohexen-1-yl)urea.

6. A method of treating hypertension in a warm-blooded animal which comprises administering to the warm-blooded animal an effective antihypertensive amount of a compound of claim 1.

7. A method of treating hypertension in a warm-blooded animal which comprises administering to the warm-blooded animal an effective antihypertensive amount of a compound of claim 2.

8. A method of treating hypertension in a warm-blooded animal which comprises administering to the warm-blooded animal an effective antihypertensive amount of the compound of claim 3.

9. A method of treating hypertension in a warm-blooded animal which comprises administering to the warm-blooded animal an effective antihypertensive amount of the compound of claim 4.

10. A method of treating hypertension in a warm-blooded animal which comprises administering to the warm-blooded animal an effective antihypertensive amount of the compound of claim 5.

11. A pharmaceutical composition comprising a pharmaceutically suitable carrier and an effective antihypertensive amount of a compound of claim 1.

12. A pharmaceutical composition comprising a pharmaceutically suitable carrier and an effective antihypertensive amount of a compound of claim 2.

13. A pharmaceutical composition comprising a pharmaceutically suitable carrier and an effective antihypertensive amount of the compound of claim 3.

14. A pharmaceutical composition comprising a pharmaceutically suitable carrier and an effective antihypertensive amount of the compound of claim 4.

15. A pharmaceutical composition comprising a pharmaceutically suitable carrier and an effective antihypertensive amount of the compound of claim 5.

* * * * *